(12) United States Patent
Higashiyama

(10) Patent No.: US 9,701,990 B2
(45) Date of Patent: Jul. 11, 2017

(54) METHOD OF CULTURING A MICROORGANISM UNDER CONTROLLED AGITATION AND AERATION CONDITIONS

(75) Inventor: Kenichi Higashiyama, Hyogo (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 1966 days.

(21) Appl. No.: 11/662,015

(22) PCT Filed: Sep. 5, 2005

(86) PCT No.: PCT/JP2005/016244
§ 371 (c)(1),
(2), (4) Date: May 28, 2008

(87) PCT Pub. No.: WO2006/028048
PCT Pub. Date: Mar. 16, 2006

(65) Prior Publication Data
US 2008/0311645 A1 Dec. 18, 2008

(30) Foreign Application Priority Data
Sep. 6, 2004 (JP) ................................. 2004-258151

(51) Int. Cl.
C12N 1/14 (2006.01)
C12P 7/64 (2006.01)

(52) U.S. Cl.
CPC .............. *C12P 7/6472* (2013.01); *C12N 1/14* (2013.01); *C12P 7/6427* (2013.01)

(58) Field of Classification Search
None
See application file for complete search history.

(56) References Cited

U.S. PATENT DOCUMENTS

| | | | |
|---|---|---|---|
| 5,322,780 A | 6/1994 | Kawashima et al. | |
| 6,280,982 B1 | 8/2001 | Kawashima et al. | |
| 6,958,229 B2 | 10/2005 | Suzuki et al. | |
| 6,985,229 B2 | 1/2006 | Lee et al. | |
| 7,709,236 B2 * | 5/2010 | Akimoto et al. | ............. 435/134 |

FOREIGN PATENT DOCUMENTS

| | | |
|---|---|---|
| JP | 49 71184 | 7/1974 |
| JP | 02-238886 | 9/1990 |
| JP | 5-91887 | 4/1993 |
| JP | 5-91888 | 4/1993 |
| JP | 06-153970 | 6/1994 |
| JP | 11-018758 | 1/1999 |
| JP | 0 957 173 | 11/1999 |
| WO | WO 98/39468 | 9/1998 |
| WO | WO 2004/033698 | 4/2004 |

OTHER PUBLICATIONS

C.M. Cooper et al., "Gas-Liquid Contractors", Ind. Chem. Eng., 1944, vol. 36, pp. 504-509.
M. Hilliger et al., "The Optimization of L-Lysine Fermentation and a Mass Transfer Model", ACTA Biotechnological, 1984, vol. 4, No. 4, pp. 355-360.
A.E. Humphrey, "Hakko Kogaku Kaishi", Journal of Fermentation Technology, 1964, vol. 42, pp. 334-345.
Satoshi Murakami et al., "Kagaku Kogaku Ronbunshu", Papers of Chemical Engineering, 2000, vol. 26, No. 4, pp. 557-562.
Peter F. Stanbury et al., "Hakkokogaku no Kiso (Principles of Fermentation Technology)", Gakkai Shuppan Senta, Translated by Ayaaki Ishizaki, 1984, pp. 172-177.
Hideo Tsujimura et al., "Scale-up of Mycelial Fermentation Based on Analysis of Fluid Velocity Distribution", Bioscience & Industry, 1994, vol. 52, No. 10, pp. 805-807.
P.R. Vilaca et al., "Determination of Power Consumption and Volumetric Oxygen Transfer Coefficient in bioreactors", Bioprocess Engineering, 2000, vol. 22, No. 3, pp. 261-265.
International Search Report dated Nov. 15, 2005 for PCT/JP2005/016244 filed Sep. 5, 2005.
Extended European Search Report dated Oct. 9, 2007 for European Appl. No. 05781593.8 mailed Oct. 9, 2007.
Badino Jr., et al., "Volumetric oxygen transfer coefficients (kLa) in batch cultivatios involving non-Newtonian broths," Biochemical Engineering Journal 8, 2001, pp. 111-119.
European Office Action dated Aug. 12, 2011, issued in European Application No. 05 781 593.8.
Higashiyama, et al., "Effects of Mineral Addition on the Growth Morphology of and Arachidonic Acid Production by *Mortierella alpina* 1S-4", JAOCS, 1998, vol. 75, No. 12, pp. 161-165.
Stanbury et al., Principles of Fermentation Technology, 2nd Ed., Butterworth-Heinemann, pp. 13 and 147-148.

* cited by examiner

*Primary Examiner* — Irene Marx
(74) *Attorney, Agent, or Firm* — Drinker Biddle & Reath LLP

(57) ABSTRACT

A method of culturing a microorganism capable of producing at least any one of a highly unsaturated fatty acid or a compound containing a highly unsaturated fatty acid as a constituent fatty acid in a culture medium containing at least a carbon source and a nitrogen source, using an aeration-agitation culture device capable of adjusting and controlling an agitation power and an aeration amount. The method comprises the steps of performing mechanical agitation for a predetermined time after start of culture, where the agitation power per unit liquid amount is 269 (W/m$^3$) or less, and after the predetermined time has passed, adjusting and controlling at least any one of the maximum aeration amount and a maximum power required for agitation to a range which satisfies that KLA $(=(P/V)^{0.95}Vs^{0.67})$ is 59 or more, an air flow rate parameter $Vs^{0.67}$ is 0.075 or more, and a required agitation power parameter $(P/V)^{0.95}$ is 203 or more, where P represents power required for agitation (W), V represents a liquid amount (m$^3$), and Vs represents an air flow rate (m/sec).

8 Claims, 1 Drawing Sheet

METHOD OF CULTURING A MICROORGANISM UNDER CONTROLLED AGITATION AND AERATION CONDITIONS

This application is the §371 national stage of PCT International Application No. PCT/JP2005/016244, filed Sep. 5, 2005, which claims priority of Japanese Patent Application No. JP2004-258151, filed Sep. 6, 2004.

BACKGROUND OF THE INVENTION

1. Field of the Invention

The present invention relates to a method of culturing a microorganism capable of producing at least any one of a highly unsaturated fatty acid and a compound containing a highly unsaturated fatty acid as a constituent fatty acid in a medium containing at least a carbon source and a nitrogen source, using an aeration-agitation culture device capable of adjusting and controlling the agitation power and the aeration amount.

2. Description of the Related Art

In aerobic culture, a result of culture (e.g., productivity of highly unsaturated fatty acid (hereinafter referred to as "PUFA (polyunsaturated fatty acid)", etc.) often varies depending on supply of oxygen. Therefore, in the case of scale-up, KLa (volumetric oxygen transfer coefficient) is considered to be an important index in addition to factors, such as the amount of aeration, agitation speed, and power required for aeration-agitation.

The use of KLa as an index in scaled-up culture is based on the idea that the same culture result is obtained irrespective of the type and scale of a culture vessel if the oxygen transfer rate is the same (see, for example, Non-patent Publications 1 and 2).

Various techniques for measuring KLa have been proposed, however, their operation is complicated. Cooper et al. has proposed a method of estimating KLa in a simpler manner, in which an approximate expression $KLa = K(P/V)^{0.95}(Vs)^{0.67}$ (K: proportionality constant, P: power required for agitation (W), V: liquid amount ($m^3$), Vs: air flow rate (m/sec)) is used (see Non-patent publication 3).

(Non-patent publication 1) Satoshi Murakami et al., Kagaku Kogaku Ronbunshu (Papers of Chemical Engineering), 26(4): 557-562 (2000)

(Non-patent publication 2) A. E. Humphery, Hakko Kogaku Kaishi (Journal of Fermentation Technology), 42: 334-345 (1964)

(Non-patent publication 3) C. M. Cooper et al., Ind. Chem. Eng., 36: 504-509 (1944)

PROBLEM TO BE SOLVED BY THE INVENTION

KLa can be predicted using the above-described approximate expression proposed by Cooper et al. However, Cooper et al. obtained a correlation between KLa and operational conditions using a 12-blade vaned disk impeller. Strictly speaking, this correlation cannot be applied to a culture vessel of a type different from that type.

Cooper et al. conducted experiments in water. Therefore, whereas the approximate expression is useful for culture of bacteria, yeast, or the like, which have a low level of rheology, the approximate expression is considered to be significantly depart from actual culture solution which contains filamentous fungi, actinomycetes, or the like, which have a high level of rheology.

The present invention is provided to solve the above-described problems. An object of the present invention is to provide a culture method capable of scale-up while securing satisfactory productivity of PUFA or a compound containing PUFA as a component without actually calculating KLa (volmetric oxygen transfer coefficient).

SUMMARY OF THE INVENTION

According to the first feature of the present invention, a method of culturing a microorganism is provided which cultures a microorganism capable of producing at least any one of a highly unsaturated fatty acid or a compound containing a highly unsaturated fatty acid as a constituent fatty acid in a culture medium containing at least a carbon source and a nitrogen source, using an aeration-agitation culture device capable of adjusting and controlling an agitation power and an aeration amount. The method comprises the steps of performing mechanical agitation for a predetermined time after start of culture, where the agitation power per unit liquid amount is 269 (W/$m^3$) or less, and after the predetermined time has passed, adjusting and controlling at least any one of the maximum aeration amount and a maximum power required for agitation to a range which satisfies that $KLA (=(P/V)^{0.95}Vs^{0.67})$ is 59 or more, an air flow rate parameter $Vs^{0.67}$ is 0.075 or more, and a required agitation power parameter $(P/V)^{0.95}$ is 203 or more, where P represents power required for agitation (W), V represents a liquid amount ($m^3$), and Vs represents an air flow rate (m/sec).

(Operational Effect)

According to the first feature of the present invention, culture can be performed using a culture medium containing at least a carbon source and a nitrogen source, and the culture medium can be consistently prepared to be uniform due to mechanical agitation. As a result, it is also possible to secure the growth of fungal cells and the reproducibility of productivity of fungal cells.

Since culture is performed in an aeration-agitation culture vessel, it is possible to efficiently culture an aerobic microorganism which produces at least any one of PUFA or a compound containing PUFA as a component (hereinafter referred to as "PUFAs").

Since the aeration-agitation culture vessel can adjust and control the agitation power and the aeration amount, the dissolved oxygen concentration of culture solution can be adjusted whenever necessary into a range which is suitable for production of PUFAs, for example.

Since mechanical agitation is performed for a predetermined time after the start of culture where the agitation power per unit liquid amount is 269 (W/$m^3$) or less (i.e., small agitation shearing stress), it is possible to suppress physical damage on hyphae and pellet-shaped fungal cells of actinomycetes and filamentous fungi. As a result, it is possible to culture these fungal cells in a form which is suitable for production of PUFAs.

After the predetermined time has passed, at least any one of the maximum aeration amount or the maximum power required for agitation is adjusted and controlled to a range which satisfies that $KLA (=(P/V)^{0.95}Vs^{0.67})$ is 59 or more, the air flow rate parameter $Vs^{0.67}$ [$(m/sec)^{0.67}$] is 0.075 or more, and the required agitation power parameter $(P/V)^{0.95}$ [$(W/m^3)^{0.95}$] is 203 or more (P: power required for agitation (W), V: liquid amount ($m^3$), Vs: air flow rate (m/sec)). Thereby, it is possible to more efficiently culture a fungus producing PUFAs. Therefore, the productivity of PUFAs can be promoted. In other words, when $KLA (=(P/V)^{0.95}Vs^{0.67})$ is smaller than 59, or when the air flow rate parameter $Vs^{0.67}$ $[(m/sec)^{0.67}]$ is smaller than 0.075, the amount of produced PUFAs (here, arachidonic acid) is small as shown in FIGS. 1 and 2. Also, a reason to set the required agitation power parameter $(P/V)^{0.95}$ $[(W/m^3)^{0.95}]$ to 203 or more is that it is intended that agitation is performed at a constant strength or more strongly than when culture is started, preferably more strongly than when culture is started (as shown in Ex. 4-2 in Table 4, the agitation power per unit liquid amount is 269 $(W/m^3)$, i.e., the required agitation power parameter $(P/V)^{0.95}$ $[(W/m^3)^{0.95}]$ is 203, at the start of culture).

In the case of scale-up, by setting the maximum aeration amount and the maximum power required for agitation based on the above-described numerical values, high-productivity culture can be performed with a minimum amount of aeration and minimum agitation power. Thereby, running cost can be reduced, resulting in scale-up with a considerably high level of production efficiency.

According to the second feature of the present invention, the highly unsaturated fatty acid is arachidonic acid.

(Operational Effect)

Arachidonic acid accounts for about 10% of fatty acids contained in an important organ, such as blood, liver, or the like (e.g., in the human blood, the ratio of fatty acids in phospholipids is as follows: arachidonic acid 11%, EPA 1%, and DHA 3%). Arachidonic acid is a major component of cell membrane and is involved in adjustment of the fluidity of the membrane to exhibit various functions in the metabolism of the body, and also plays an important role as a direct precursor of prostaglandins.

Particularly at recent, arachidonic acid has attracted attention because of a role of nutrition for suckling infants and as a constituent fatty acid of endogenous-cannabinoid (2-arachidonoyl monoglycerol, anandamide), which exhibits an bility to activate nerves.

Linoleic acid taken from linoleic acid-rich food is usually converted to arachidonic acid. However, in adult disease patients or potential patients, suckling infants, and elders, the function of an enzyme(s) involved in biosynthesis is lowered, likely leading to lack of arachidonic acid. Therefore, it is desirable that arachidonic acid be directly taken as fat or oil (a constituent fatty acid of triglyceride).

According to the second feature of the present invention, it is possible to efficiently and stably produce at least any one of arachidonic acid, which plays an important role for nutrition of suckling infants, or a compound (e.g., fats, oils, etc.) containing arachidonic acid as a constituent fatty acid. Therefore, the present invention may contribute to maintenance or promotion of public health via beverages, therapeutic nutrient foods, feeds, pharmaceuticals, and the like which contain these materials.

According to the third feature of the present invention, the fungus producing PUFAs is of the genus *Mortierella*, subgenus *Mortierella*.

(Operational Effect)

According to the third feature of the present invention, by using a fungus producing PUFAs of the genus *Mortierella*, subgenus *Mortierella*, it is possible to produce PUFAs more efficiently, and in addition, the fungi can be easily obtained, as described below and elsewhere herein.

According to the fourth aspect of the present invention, the predetermined time after the start of culture is preferably 12 to 24 hours.

(Operational Effect)

According to the fourth feature of the present invention, mechanical agitation having a low level of agitation shearing stress (specifically, agitation power per unit liquid amount is 269 $(W/m^3)$ or less) is performed for 12 to 24 hours after the start of culture. During this period, a fungus which transforms from a pulp-shaped hypha to a pellet-shaped cell can be caused to efficiently perform such transformation, thereby suppressing a significant increase in the viscosity of subsequent culture solution. Therefore, it is possible to more efficiently produce PUFAs.

DESCRIPTION OF THE PREFERRED EMBODIMENTS (Embodiments)

Figure 1:
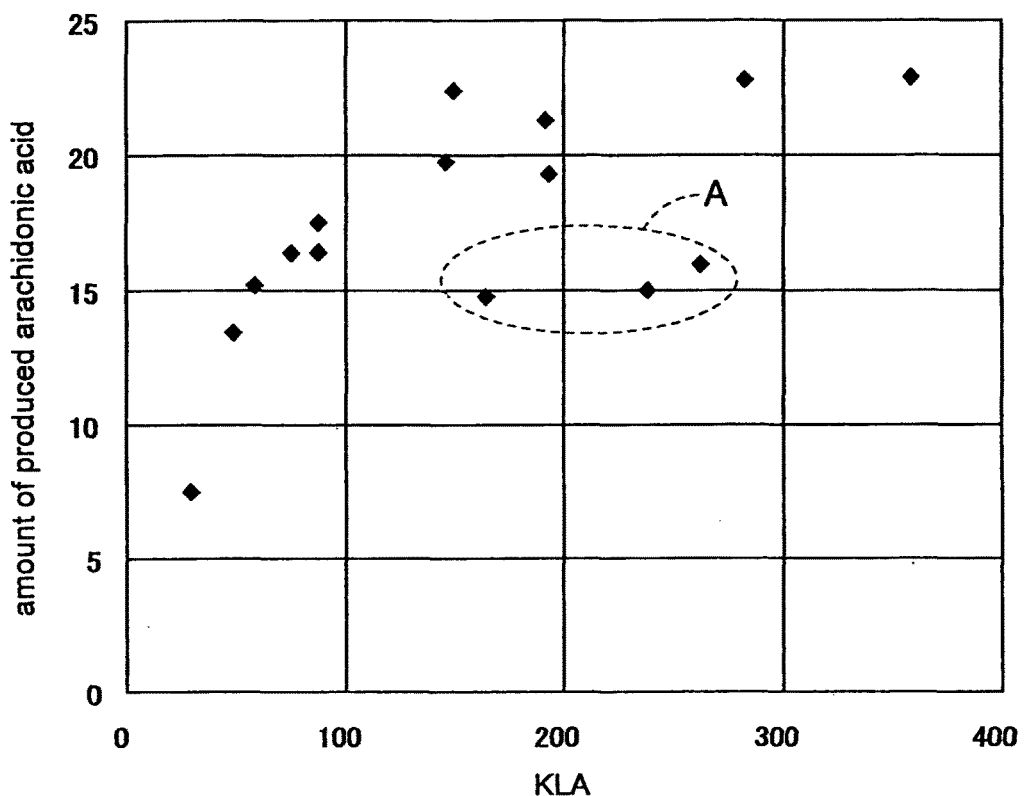
FIG. 1 is a plot indicating a relationship between the amount of produced arachidonic acid and a KLA value which were obtained in cultures.

Examples of a microorganism for use in the present invention which has ability to produce at least any one of PUFA or a compound containing PUFA as a constituent fatty acid (e.g., fat or oil (triglyceride) and/or phospholipid) include the genus *Mortierella*, the genus *Conidiobolus*, the genus *Pythium*, the genus *Phytophthora*, the genus *Penicillium*, the genus *Cladosporium*, the genus *Mucor*, the genus *Fusarium*, the genus *Aspergillus*, the genus *Rhodotorula*, the genus *Entomophthora*, the genus *Echinosporangium*, and the genus *Saprolegnia*.

Particularly, examples of the microorganisms belonging to the genus *Mortierella*, subgenus *Mortierella* include *Mortierella elongata*, *Mortierella exigua*, *Mortierella hygrophila*, *Mortierella alpina*, and the like. Specifically, fungal strains of *Mortierella elongate* IFO8570, *Mortierella exigua* IFO8571, *Mortierella hygrophila* IFO5941, *Mortierella alpina* IFO8568, ATCC16266, ATCC32221, ATCC42430, CBS219.35, CBS224.37, CBS250.53, CBS343.66, CBS527.72, CBS529.72, CBS608.70, CBS754.68, and the like can be illustrated.

Any of these fungal strains are available without limitation from Institute of Fermentation, Osaka (IFO), American Type Culture Collection (ATCC), or Centrralbureau voor Schimmelcultures (CBS). In addition, *Mortierella elongate* SAM0219 (FERM P-8703) (FERM BP-1239), and *Mortierella alpina* 1S-4, which were isolated from soil by the research group of the present invention, can be used. *Mortierella elongata* SAM 0219 is internationally deposited under the Budapest Treaty with accession number FERM BP-1239 at International Patent Organism Depositary (IPOD), Japan.

A fungal strain for use in the present invention is cultured (main culture) by inoculating a spore or a hypha of the fungal strain, or a seed culture solution obtained by preliminary culture, or a fungal cell recovered from the seed culture onto liquid culture medium. In the case of liquid culture medium, as the carbon source, any of those which are commonly used, such as glucose, fructose, xylose, saccharose, maltose, soluble starch, molasses, glycerol, mannitol, saccharified starch, and the like, can be used. The present invention is not limited to these. As the nitrogen source, naturally-occurring nitrogen sources (e.g., peptone, yeast extract, malt extract, meat extract, casamino acid, corn steep liquor, soybean protein, defatted soybean, cottonseed meal, etc.), organic nitrogen sources (e.g., urea, etc.), and inorganic nitrogen sources (e.g., sodium nitrate, ammonium nitrate, ammonium sulfate, etc.) can be used. Particularly, specific examples of a nitrogen source obtained from soybean include soybean, defatted soybean, soybean flake, edible soybean protein, soybean meal, bean curd, soy flour, and the like. Particularly, defatted soybean which is denatured by heat, more preferably defatted soybean which is treated by heating at about 70 to 90° C., followed by removal of ethanol soluble components, can be used singly or multiply, or in combination with the above-described nitrogen sources.

Further, metal ions (e.g., iron, copper, zinc, manganese, nickel, cobalt, etc.), vitamins, and the like can be optionally used as a small amount of nutrient source in addition to phosphate ion, potassium ion, sodium ion, magnesium ion, and calcium ion. These culture medium ingredients are not particularly limited if they have a concentration which does not inhibit the growth of a microorganism. In practical use, the total amount of added carbon source(s) is generally 0.1 to 40% by weight, preferably 1 to 25% by weight, and the total amount of added nitrogen source(s) is 2 to 15% by weight, preferably 2 to 10% by weight. More preferably, the starting amount of added carbon source(s) is 1 to 5% by weight, and the starting nitrogen source concentration is 3 to 8% by weight, and a carbon source(s) and a nitrogen source(s) are added at some point(s) during culture (more preferably, only a carbon source(s) is added).

Note that, in order to increase the yield of unsaturated fatty acid, hydro carbon, such as hexadecane or octadecane; fatty acid, such as oleic acid or linoleic acid, or a salt or a fatty acid ester thereof (e.g., ethyl ester, glycerin fatty acid ester, sorbitan fatty acid ester); or fats and oils, such as olive oil, soybean oil, rape oil, cottonseed oil, or coconut oil, can be used as precursors of unsaturated fatty acid, singly or in combination. The added amount of these substrates is 0.001 to 10% with respect to culture medium, preferably 0.5 to 10%. These substrates may serve as the only carbon source for culture.

In the present invention, culture temperature varies depending on microorganisms used. For example, the culture temperature is 5 to 40° C., preferably 20 to 30° C. Alternatively, microorganisms can be cultured and grown at 20 to 30° C., followed by culture at 5 to 20° C. to produce unsaturated fatty acid. By such a temperature control, the proportion of highly unsaturated fatty acid in the produced fatty acid can be increased.

Aeration-agitation culture, shaking culture, solid culture, or still liquid culture is performed in seed culture, while aeration-agitation culture is performed in main culture. At the start of the main culture (at the time of inoculating seed culture solution), the pH of culture medium is adjusted to 5 to 7, preferably 5.5 to 6.5. The period of the main culture is usually 2 to 30 days, preferably 5 to 20 days, and more preferably 5 to 15 days.

The culture method of the present invention is performed using an aeration-agitation culture device which can adjust and control the agitation power and the aeration amount, and is equipped with a culture vessel and an agitation impeller, where the ratio (d/D) of the diameter of the agitation blade (=d)) to the diameter of the culture vessel (=D) is 0.30 to 0.6, preferably 0.34 to 0.55, more preferably 0.37 to 0.55, and most preferably 0.42 to 0.55.

It is known that microorganisms belonging to the genus *Mortierella*, subgenus *Mortierella* can produce a fat or an oil (triglyceride) having arachidonic acid as a major constituent fatty acid. The present inventors have obtained a microorganism capable of producing fat or oil (triglyceride) having dihomo-γ-linoleic acid as a major constituent fatty acid (JP H05-91887 A) and a microorganism capable of producing a fat or an oil (triglyceride) having ω9 highly unsaturated fatty acid as a major constituent fatty acid (JP H05-91888 A) by introducing mutation into the above-described fungal strain. The present inventors have also obtained a microorganism resistant to a high-concentration carbon source (WO98/39468). These microorganisms belong to the genus *Mortierella*, subgenus *Mortierella*, and the productivity thereof can be improved by culture using the culture method of the present invention.

An outline of a culture process of the main culture which employs the above-described microorganism, culture medium, and culture device will be described.

At the start of culture, the culture is conducted while performing relatively weak mechanical agitation (agitation power per unit liquid amount: 269 (W/m$^3$) or less), and aeration.

In this case, the amount of aeration is not particularly limited. When actinomycetes or filamentous fungi are cultured in liquid under aerobic conditions, the microorganisms may change their forms from a pulp-shaped hypha to a pellet-shaped fungal cell (also called as a spherical hypha) when going from the vegetative phase to the productive phase.

As used herein, the pellet-shaped fungal cell refers to one fungal form of actinomycetes and filamentous fungi when cultured in liquid culture medium, specifically indicating a spherical or spindle-shaped hypha aggregation having an average diameter of 0.2 to several millimeters.

As used herein, the pulp-shaped hypha refers to a typical fungal form of actinomycetes and filamentous fungi when cultured in liquid culture medium, specifically indicating that linearly or radially elongated hyphae distributed. The transformation from the pulp-shaped hypha to the pellet-shaped fungal cell is closely related with the productivity of PUFAs.

If mechanical agitation having high agitation shearing stress destroys the pellet-shaped fungal form or interferes with transformation to the pellet-shape, the viscosity of culture solution increases with the growth of fungal cells, leading to a reduction in mixing efficiency. As a result, it is considered that oxygen or the like is not likely to be supplied sufficiently to fungal cells, leading to a reduction in the productivity of PUFAs.

Conventionally, in order to promote transformation to the pellet-shape, an optimum culture medium composition is studied or the partial pressure of oxygen in aeration gas is adjusted. In the present invention, agitation having low agitation shearing stress is performed for a predetermined time from the start of culture, thereby promoting transformation of fungal cells to the pellet-shape.

The aeration-agitation device is equipped with a dissolved oxygen concentration detecting sensor to monitor the dissolved oxygen concentration of culture solution.

The dissolved oxygen concentration (DO) of culture medium starts to decrease with the growth of fungal cells. However, the agitation power and the amount of aeration are increased immediately before the DO value reaches the lower limit (about 50%) above which the productivity of PUFAs is not influenced, thereby adjusting and maintaining the DO value.

A time required to reach the lower limit of the DO value is about 12 to 24 hours after the start of culture. Thereafter, culture is performed while adjusting and controlling at least one of the maximum aeration amount or the maximum power required for agitation to a range which satisfies that KIA ($=(P/V)^{0.95}Vs^{0.67}$) is 59 or more, the air flow rate parameter $Vs^{0.67}$ [unit: $(m/sec)^{0.67}$] is 0.075 or more, and the required agitation power parameter $(P/V)^{0.95}$ [unit: $(W/m^3)^{0.95}$] is 203 or more. As a specific example of the adjustment and control, it is considered that either or both of the maximum aeration amount and the maximum power required for agitation are increased.

As used herein, the KIA value refers to a parameter which is newly introduced by the present inventors based on the Cooper et al's approximate expression KLa (volmetric oxygen transfer coefficient)=$K(P/V)^{0.95}(Vs)^{0.67}$. It was found for the first time by the present inventors that there is a satisfactorily positive correlation between the KLA value and the amount of produced PUFAs.

About 40 to 48 hours after the start of culture, nutrient(s) (particularly, a nitrogen source) in culture medium are exhausted and the fungal cell concentration reaches the highest value, and the fungal cell transforms from the vegetative phase to the phase of producing PUFAs, in which accumulation of PUFAs is promoted in the fungal cell.

Thereafter, culture is performed for 5 to 15 days while adding glucose culture medium whenever necessary during culture. After the end of culture, the fungal cells are recovered and dried, followed by hexane extraction of the dried fungal cells to obtain at least any one of PUFA and a compound (e.g., triglyceride, phospholipid, etc.) containing PUFA as a constituent fatty acid.

EXAMPLES

Example 1

Measurement of Power Required for Agitation

Tap water (6 kL (=V)) was placed in a 10-kL capacity aeration-agitation culture vessel. Agitation power consumption (=A) was measured under aeration of 1 vvm when agitation is performed at various agitation rotational speeds. Next, no-load operation was performed with the same rotational speeds in the same vessel, and agitation power consumption was measured (=B). During no-load operation, in order to prevent the agitation shaft from overheating, water was placed up to a level such that the water surface was lower than the agitation impeller, and the lower bearing portion of the agitation shaft was immersed in the water.

Effective power was measured using a power meter (clamp-on power meter manufactured by Hioki E. E. Corporation) which was provided on a first-order side (power source side) of an inverter.

A value obtained by subtracting the value B from the value A is assumed to be power required for agitation (=P). The value P is divided by a liquid amount to obtain power required for agitation per liquid amount (=P/V). Actually measured values thus calculated are shown in a table below.

TABLE 1

| agitation rotational speed (rpm)(=N) | power consumption when water was placed (kW) (=A) | power consumption during no-load operation (kW) (=B) | power required for agitation (kW) (P = A · B) | power required for agitation per liquid amount $(kW/m^3)$ (P/V) |
|---|---|---|---|---|
| 35 | 1.660 | 0.630 | 1.030 | 0.172 |
| 65 | 6.804 | 1.050 | 5.754 | 0.959 |
| 95 | 17.528 | 1.498 | 16.030 | 2.672 |

The actually measured values were plotted on a graph where the horizontal axis indicates the agitation rotational speed (=N), while the vertical axis indicates the power required for agitation per liquid amount (=P/V), and parameters X and Y of an approximate expression $P/V=XN^Y$ were obtained by the least square method. The values X and Y and the approximate expression thus obtained were used to calculate power required for agitation per unit liquid amount with respect to an arbitrary agitation rotational speed.

When aeration to the culture vessel was stopped, an increase in the power required for agitation was observed. Using a method similar to that described above, the values X and Y were obtained in the absence of aeration, and the power required for agitation per liquid amount was calculated with respect to an arbitrary agitation rotational speed.

Example 2

Power Required for Agitation of Culture Solution

An arachidonic acid producing fungus, *Mortierella alpina* strain 1S-4, was cultured in a 10-kL culture vessel. Agitation power consumption was measured in 6 kL of culture solution and under aeration of 1 vvm when agitation was performed with various agitation rotational speeds. The results are shown in a table below.

TABLE 2

| agitation rotational speed (rpm) (=N) | power consumption when water was placed (kW) (=A) |
|---|---|
| 35 | 1.720 |
| 65 | 6.700 |
| 95 | 17.612 |

By comparing the agitation power obtained in Examples 1 and 2, it was confirmed that the agitation power is not significantly different between when operation was performed where water was placed (Example 1) and when operation was performed where culture solution was placed (Example 2). Therefore, it was considered that the power required for agitation during culture can be approximated with the power required for agitation obtained when operation was performed in the same culture vessel where water was placed.

Example 3

Suspension of spores of *M. alpina* strain 1S-4 was inoculated to a concentration of 0.1% by volume (vol %) into a culture medium containing 1.0% yeast extract and 2.0% glucose and having a pH of 6.3. Seed culture was started with reciprocal shaking at 100 rpm at a temperature of 28° C. (first stage), and was performed for 3 days.

Next, 30 L of a culture medium containing 1% yeast extract, 2% glucose, 0.1% soybean oil, and having a pH of 6.3 was prepared in a 50-L capacity aeration-agitation culture vessel. The culture medium was inoculated with the seed culture (first stage) solution, and seed culture (second state) was started where the agitation rotational speed was 200 rpm, the temperature was 28° C., and the vessel pressure was 150 kPa, and was performed for 2 days.

Next, a culture medium for main culture was prepared in a 10-kL capacity aeration-agitation vessel (the inner diameter of the culture vessel is 1.8 m). The culture medium was prepared in the following manner. Initially, 4500 L of a culture medium (culture medium A: soybean flour 336 kg; $KH_2PO_4$ 16.8 kg; $MgCl_2.6H_2O$ 2.8 kg; $CaCl_2.2H_2O$ 2.8 kg; soybean oil 5.6 kg) was prepared to pH 4.5, and was sterilized in the main culture vessel at 121° C. for 20 minutes. 1000 L of another culture medium (culture medium B: water-containing glucose 112 kg) was sterilized in another culture vessel at 121° C. for 20 minutes, and was then sterilely transferred to the main culture vessel to be added to the culture medium A (the culture medium after addition is referred to as a culture medium C). Sterilized aqueous sodium hydroxide solution was sterilely added to the culture medium C and was adjusted to pH 6.1, and thereafter, the seed culture solution (second stage) having a volmetric capacity of 28 L was inoculated to the culture medium C by sterile manipulation, resulting in a total of 5600 L (starting culture liquid amount) (the culture vessel has a volmetric capacity of 10 kL). Culture was started where the temperature was 26° C., the internal pressure was 200 kPa, the amount of aeration was 49 m³/hr (air flow rate (=Vs) was 0.00535 m/sec), the power required for agitation per liquid amount (=P/V) was 112 W/m³. Values of the parameters at the time of start of the culture were calculated as follows.

$$(P/V)^{0.95}:89[(W/m^3)^{0.95}]$$

$$Vs^{0.67}:0.03[(m/sec)^{0.67}]$$

$$KLA(=(P/V)^{0.95}Vs^{0.67}):2.67[(W/m^3)^{0.95}\cdot(m/sec)^{0.67}] \quad \text{(Expression 1)}$$

The agitation power (=P/V) was changed to 880 W/m³ at hour 15 of culture, and the amount of aeration and the agitation rotational speed were gradually increased until the aeration amount was 437 m³/hr (air flow rate (=Vs): 0.0477 m/sec) and the agitation power (=P/V) was 3250 W/m³, by hour 40 of the culture. Values of the parameters at the high aeration-agitation level were calculated as follows.

$$(P/V)^{0.95}: 2169[(W/m^3)^{0.95}]$$

$$Vs^{0.67}:0.130[(m/sec)^{0.67}]$$

$$KLA(=(P/V)^{0.95}Vs^{0.67}):282[(W/m^3)^{0.95}\cdot(m/sec)^{0.67}] \quad \text{(Expression 2)}$$

The main culture was performed for 306 hours while adding culture medium at some point(s) during culture as described below. At the end of the culture, the culture liquid amount was 7750 L due to the addition (increase) and the evaporation (decrease) of culture medium.

TABLE 3

| main culture time | added culture medium |
|---|---|
| after 19 hours | water-containing glucose 280 kg/460 L |
| after 43 hours | water-containing glucose 280 kg/450 L |
| after 67 hours | water-containing glucose 252 kg/390 L |
| after 91 hours | water-containing glucose 252 kg/410 L |
| after 120 hours | water-containing glucose 224 kg/370 L |
| after 140 hours | water-containing glucose 168 kg/280 L |
| after 163 hours | water-containing glucose 168 kg/270 L |

After the culture, sterilization was performed at 120° C. for 20 minutes, and thereafter, the wet fungal cells were recovered using a continuous hydroextractor, followed by drying with hot air (hot air temperature: 120° C.) using a shaking fluid bed dryer to a water content of 2% by weight (wt %). The dried fungal cell was cooled to 40° C. in a fluid bed by supply of room air, and was then transported to a loading place using a pneumatic conveyor. The resultant dried fungal cell was loaded along with nitrogen gas into an aluminum container bag (pouch) having a volmetric capacity of about 1 m³, and the mouth of the bag was sealed by heat. The bag was preserved at 10° C. or less in a refrigerator.

The dried fungal cell removed from the container bag was subjected to hexane extraction. The hexane solution was filtered to remove solid components thereof. Thereafter, the resultant solution was heated under reduced pressure to remove hexane, thereby obtaining crude oil having arachidonic acid as a constituent fatty acid.

Example 4

Influence of Power Required for Agitation at Start of Culture

Seed culture was performed and a culture medium for main culture was prepared using a method similar to that of Example 3. The main culture was performed under the same conditions as those of Example 3, except that conditions for agitation at the start of culture were set to be various values as shown in a table below.

According to the result of the culture, it was found that the P/V value at the start of the culture has a significant level of influence on production of arachidonic acid.

TABLE 4

| | conditions at start of culture required agitation power per liquid amount at start of culture P/V (W/m³) | parameter $(P/V)^{0.95}$ $[(W/m^3)^{0.95}]$ | result of culture amount of produced arachidonic acid per amount of culture solution (*) (g/L) |
|---|---|---|---|
| experiment No. | | | |
| Ex. 4-1 | 41 | 34 | 22.4 |
| Ex. 4-2 | 269 | 203 | 22.40 |
| Ex. 4-3 | 810 | 579 | 17.0 |
| Ex. 4-4 | 3250 | 2169 | 14.1 |
| Ex. 3 (example 3) | 112 | 89 | 22.8 |

(*) values are corrected by the following expression since the amount of culture solution varies from culture to culture, depending on evaporation and glucose addition.

Amount of produced arachidonic acid(corrected value)=amount of produced arachidonic acid per culture solution at end of culture×liquid amount at end of culture/liquid amount at start of culture         (Expression 3)

Example 5

Influence of Amount of Aeration at Start of Culture

Seed culture was performed and a culture medium for main culture was prepared using a method similar to that of Example 3. The main culture was performed under the same conditions as those of Example 3, except that conditions for aeration at the start of culture were set to be various values as shown in a table below. In both experiments Exs. 5-1 and 5-2, since the amount of aeration was set to be high from the start of culture, a considerably high level of tendency to produce bubbles was observed as compared to Ex. 3 until hour 20 of the culture after the start. Therefore, a method of stopping aeration intermittently was adopted in order to suppress bubbling.

When aeration was performed, bubbling occurred and the height of bubbles started increasing. Aeration in the solution was stopped immediately after the height of bubbles rose near the ceiling of the vessel (near an exhaust line). When aeration was stopped, the height of bubbles started falling, and at the same time, the dissolved oxygen concentration (DO) of the culture solution also started decreasing. Aeration was started again immediately before the DO value reached at the lower limit above which the productivity of arachidonic acid is not influenced. Similar operations were repeated until the tendency to bubble substantially disappeared. An air flow rate Vs in Example 5 is an air flow rate when aeration is being performed, but not an average accumulated amount of aeration obtained taking the intermittent aeration in account. The lower limit of the DO value above which the productivity of arachidonic acid is not influenced is a DO concentration (critical DO concentration) below which a lineal relationship between a decrease in DO due to the stop of aeration and an elapsed time is lost. The critical DO concentration was previously obtained using a dynamic measuring method ("Hakkokogaku no Kiso (Principles of Fermentation Technology)", 1988, Gakkai Shuppan Senta, translated by Ayaaki Ishizaki), where culture was performed under the same conditions.

According to the result of the culture, it was confirmed that the Vs value at the start of culture has substantially no influence on production of arachidonic acid.

TABLE 5

| experiment No. | conditions at start of culture air flow rate at start of culture Vs (m/sec) | parameter $Vs^{0.67}$ [$(m/sec)^{0.67}$] | result of culture amount of produced arachidonic acid per amount of culture solution (*) (g/L) |
|---|---|---|---|
| Ex. 5-1 | 0.0196 | 0.0719 | 22.3 |
| Ex. 5-2 | 0.0477 | 0.130 | 22.6 |
| Ex. 3 (example 3) | 0.00535 | 0.0301 | 22.8 |

(*) values are corrected by the following expression since the amount of culture solution varies from culture to culture, depending on evaporation and glucose addition.

Amount of produced arachidonic acid(corrected value)=amount of produced arachidonic acid per culture solution at end of culture×liquid amount at end of culture/liquid amount at start of culture (Expression 4)

Example 6

Influence of Highest KLA Value

Seed culture was performed and a culture medium for main culture was prepared using a method similar to that of Example 3. Culture was started where the temperature was 26° C., the internal pressure was 200 kPa, the amount of aeration was 49 m³/hr (air flow rate (=Vs) was 0.00535 m/sec), and the power required for agitation per culture liquid amount (=P/V) was 112 W/m³ as in Example 3. Values of the parameters at the time of start of culture were calculated as follows.

$(P/V)^{0.95}$:89[$(W/m^3)^{0.95}$]

$Vs^{0.67}$:0.03[$(m/sec)^{0.67}$]

$KLA(=(P/V)^{0.95}Vs^{0.67})$:2.67[$(W/m^3)^{0.95}\cdot(m/sec)^{0.67}$] (Expression 5)

Figure 2:
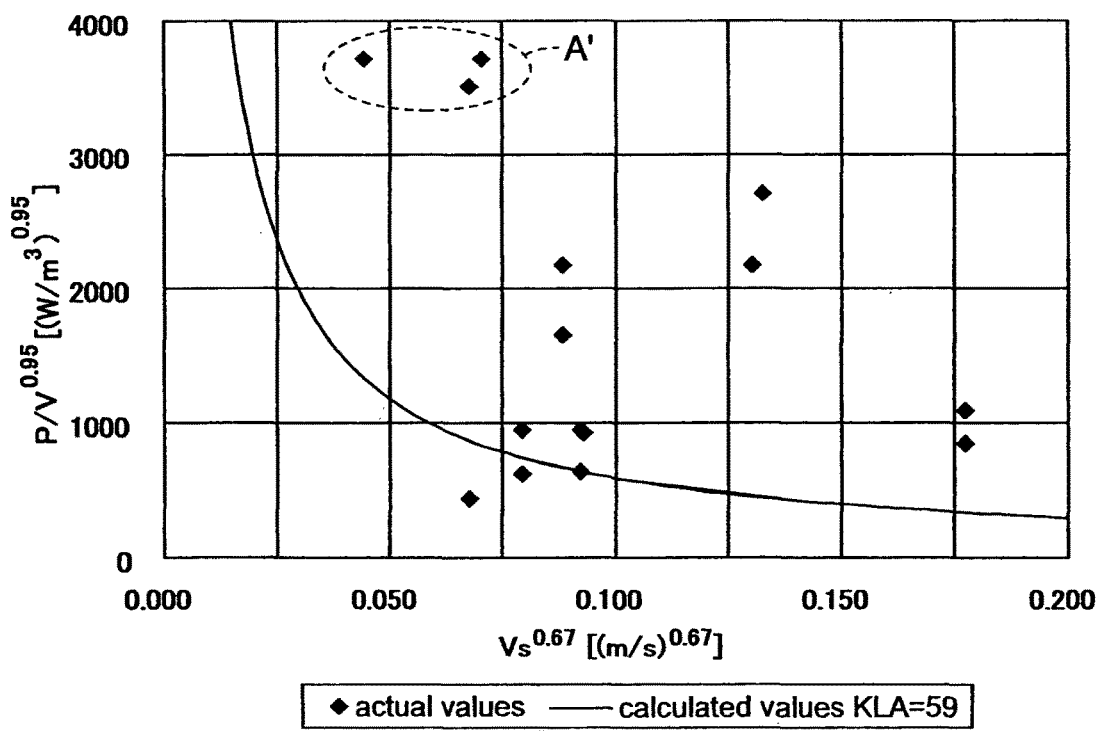
FIG. 2 is a plot indicating a correlation between two parameters constituting the KLA value, i.e., $(P/V)^{0.95}$ value and $Vs^{0.67}$ value.

The power required for agitation (=P/V) was changed to 380 W/m³ at hour 18 of the culture, and thereafter, the amount of aeration and the agitation rotational speed were gradually increased by hour 48 of the culture. The culture was performed under various maximum aeration amount and highest agitation power conditions. FIG. 1 is a plot indicating a relationship between the amount of produced arachidonic acid in each culture and the highest KLA $(=(P/V)^{0.95}Vs^{0.67})$ value. According to this plot, it was found that there is a satisfactorily positive correlation between the KIA value and the amount of produced arachidonic acid. In FIG. 1, it was also found that there were some cases in which the amount of produced arachidonic acid was as small as about 15 to 16 g/L even if the KLA value was increased to 100 or more (e.g., points within a range indicated with A in FIG. 1), and there were also some cases which departed from the correlation between the KIA and the amount of produced arachidonic acid. To examine the reason, a plot of the two parameters, the $(P/V)^{0.95}$ value and the $Vs^{0.67}$ value, which constitute the KLA value, was produced (FIG. 2). In this case, points within a range indicated with A' in FIG. 2 correspond to the points within the range indicated with A in FIG. 1. As a result, it was found that if the KLA value is high, but the $Vs^{0.67}$ value is not 0.075 or more, the increase of the KLA value does not lead to the effect of increasing the amount of produced arachidonic acid.

Example 7

Seed culture was performed in a manner similar to that of Example 3. 1300 L of a culture medium for main culture having the same ingredient concentrations as those of Example 3 was prepared in a 2-kL capacity culture vessel. Culture was started where the temperature was 26° C., the internal pressure was 200 kPa, the air flow rate was 0.0087 (m/sec), and the power required for agitation per culture liquid amount (=P/V) was 264 W/m³. Values of the parameters at the time of start of culture were calculated as follows.

$(P/V)^{0.95}$:199[$(W/m^3)^{0.95}$]

$Vs^{0.67}$:0.042[$(m/sec)^{0.67}$]

$KLA(=(P/V)^{0.95}Vs^{0.67})$:8.28[$(W/m^3)^{0.95}\cdot(m/sec)^{0.67}$] (Expression 6)

The power required for agitation (=P/V) was changed to 890 W/m³ at hour 24 of the culture, and thereafter, the amount of aeration and the agitation rotational speed were gradually increased until the air flow rate Vs was 0.084 (m/sec) and the agitation power P/V was 1493 W/m³, by hour 48 of the culture. Values of the parameters at the high aeration-agitation level were calculated as follows.

$(P/V)^{0.95}$:1036[$(W/m^3)^{0.95}$]

$Vs^{0.67}$:0.191[$(m/sec)^{0.67}$]

$KLA(=(P/V)^{0.95}Vs^{0.67})$:198[$(W/m^3)^{0.95}\cdot(m/sec)^{0.67}$] (Expression 7)

The main culture was performed for 306 hours while adding glucose having the same concentration as that of Example 3 at some point(s) during the culture. As a result, 20.0 g/L of produced arachidonic acid (corrected value) was obtained.

Example 8

*Mortierella alpina* strain CBS754.68 was used as an arachidonic acid producing fungus. The preserved fungal strain was used to perform seed culture and a culture medium for main culture was prepared using a method similar to that of Example 3. Culture was started where the temperature was 26° C., the internal pressure was 200 kPa, the amount of aeration was 49 m³/hr (air flow rate (=Vs) was 0.00535 m/sec), and the power required for agitation per culture liquid amount (=P/V) was 112 W/m³. Values of the parameters at the time of start of culture were calculated as follows.

$$(P/V)^{0.95}: 89[(W/m^3)^{0.95}]$$

$$Vs^{0.67}: 0.03[(m/sec)^{0.67}]$$

$$KLA(=(P/V)^{0.95}Vs^{0.67}): 2.67[(W/m^3)^{0.95} \cdot (m/sec)^{0.67}] \quad \text{(Expression 8)}$$

Culture was started under these conditions, and the starting agitation rotational speed was changed at different times, so that culture was performed a plurality of times (experiment Nos. Ex. 6-1 to 6-4). When the starting agitation rotational speed was changed for the first time, the agitation power (=P/V) was changed to 380 W/m³, and thereafter, the amount of aeration and the agitation rotational speed were gradually increased until the maximum aeration amount was 437 m³/hr (air flow rate (=Vs): 0.0477 m/sec) and the maximum agitation power (=P/V) was 3250 W/m³, by hour 48 of the culture. Values of the parameters at the high aeration-agitation level were calculated as follows.

$$(P/V)^{0.95}: 2169[(W/m^3)^{0.95}]$$

$$Vs^{0.67}: 0.130[(m/sec)^{0.67}]$$

$$KLA(=(P/V)^{0.95}Vs^{0.67}): 282[(W/m^3)^{0.95} \cdot (m/sec)^{0.67}] \quad \text{(Expression 9)}$$

The main culture was performed for 288 hours while adding glucose at some point(s) during the culture as in Example 3.

As a result of the culture, it was found that the time at which the agitation power was changed for the first time after the start of the culture has a significant influence on production of arachidonic acid.

TABLE 6

| experiment No. | first agitation power changing time (elapsed time from start of culture (inoculation of seed culture)) | result of culture (*) amount of produced arachidonic acid per amount of culture solution (g/L) |
|---|---|---|
| Ex. 6-1 | 6 hr | 10.1 |
| Ex. 6-2 | 12 hr | 18.5 |
| Ex. 6-3 | 24 hr | 18.7 |
| Ex. 6-4 | 30 hr | 9.5 |

(*) values are corrected by the following expression since the amount of culture solution varies from culture to culture, depending on evaporation and glucose addition.

Amount of produced arachidonic acid(corrected value)=amount of produced arachidonic acid per culture solution at end of culture×liquid amount at end of culture/liquid amount at start of culture  (Expression 10)

Example 9

Production of DGLA

Mortierella alpina strain SAM1860 was used as a dihomo-γ-linoleic acid producing fungus. The preserved fungal strain was inoculated into a culture medium containing 1% yeast extract and 2% glucose and having a pH of 6.3, which was prepared in a flask, followed by seed culture (first stage) at 100 rpm at 28° C. for 3 days. Next, 30 L of a culture medium containing 1% yeast extract, 2% glucose, and 0.1% soybean oil and having a pH of 6.3 was prepared in a 50-L capacity aeration-agitation culture vessel, and was inoculated with the culture solution previously obtained by the seed culture (first stage), followed by seed culture (second stage) for 2 days where the agitation rotational speed was 200 rpm, the temperature was 28° C., and the vessel internal pressure was 150 kPa.

Next, a culture medium containing 4% defatted soybean flour, 1.8% glucose, 0.3% $KH_2PO_4$, 0.1% $Na_2SO_4$, 0.05% $MgCl_2 \cdot 6H_2O$, 0.05% $CaCl_2 \cdot 2H_2O$, and 0.1% soybean oil and having a pH of 6.1 was inoculated with 0.5% of the seed culture solution (second stage). Main culture was started with 4000 L (liquid amount) of the culture medium.

The culture was started where the temperature was 26° C., the internal pressure was 200 kPa, the amount of aeration was 52 m³/hr (air flow rate (=Vs) was 0.0057 m/sec), and the power required for agitation per culture liquid amount (=P/V) was 30 W/m³. Values of the parameters at the time of start of culture were calculated as follows.

$$(P/V)^{0.95}: 25[(W/m^3)^{0.95}]$$

$$Vs^{0.67}: 0.0313[(m/sec)^{0.67}]$$

$$KLA(=(P/V)^{0.95}Vs^{0.67}): 0.782[(W/m^3)^{0.95} \cdot (m/sec)^{0.67}] \quad \text{(Expression 11)}$$

Culture was started under these conditions. The agitation power was changed at hour 19 of culture after the start of the culture, and the amount of aeration and the agitation rotational speed were gradually increased until the maximum aeration amount was 240 m³/hr (air flow rate (=Vs): 0.0262 m/sec) and the maximum agitation power (=P/V) was 1251 W/m³, by hour 48 of the culture. Values of parameters at a high aeration-agitation level were calculated as follows.

$$(P/V)^{0.95}: 875.9[(W/m^3)^{0.95}]$$

$$Vs^{0.67}: 0.0871[(m/sec)^{0.67}]$$

$$KLA(=(P/V)^{0.95}Vs^{0.67}): 76.3[(W/m^3)^{0.95} \cdot (m/sec)^{0.67}] \quad \text{(Expression 12)}$$

The main culture was performed for 160 hours while adding glucose at some point(s) during the culture. As a result, the concentration of produced dihomo-γ-linoleic acid was 7.0 g/L at the end of culture.

Example 10

Production of Mead Acid

Mortierella alpina strain SAM2086 was used as a mead acid producing fungus. The preserved fungal strain was inoculated into a culture medium containing 1% yeast extract and 2% glucose and having a pH of 6.3, which was prepared in a flask, followed by seed culture (first stage) at 100 rpm at 28° C. for 3 days. Next, 30 L of a culture medium containing 1% yeast extract, 2% glucose, and 0.1% olive oil and having a pH of 6.3 was prepared in a 50-L capacity aeration-agitation culture vessel, and was inoculated with the culture solution previously obtained by the seed culture (first stage), followed by seed culture (second stage) for 2 days where the agitation rotational speed was 200 rpm, the temperature was 28° C., and the vessel internal pressure was 150 kPa.

Next, a culture medium containing 4% defatted soybean flour, 1.8% glucose, 0.3% $KH_2PO_4$, 0.1% $Na_2SO_4$, 0.05% $MgCl_2 \cdot 6H_2O$, 0.05% $CaCl_2 \cdot 2H_2O$, and 0.1% olive oil, and having a pH of 6.1 was inoculated with 0.5% of the seed culture solution (second stage). Main culture was started with 4000 L (liquid amount) of the culture medium.

The culture was started where the temperature was 24° C., the internal pressure was 200 kPa, the amount of aeration was 52 m$^3$/hr (air flow rate (=Vs) was 0.0057 m/sec), and the power required for agitation per culture liquid amount (=P/V) was 30 W/m$^3$. Values of the parameters at the time of start of culture were calculated as follows.

$$(P/V)^{0.95}:25[(W/m^3)^{0.95}]$$

$$Vs^{0.67}: 0.0313[(m/sec)^{0.67}]$$

$$KLA(=(P/V)^{0.95}Vs0.67): \\ 0.782[(W/m^3)^{0.95} \cdot (m/sec)^{0.67}] \quad \text{(Expression 13)}$$

The culture was started under these conditions. The agitation power was changed at hour 22 of culture after the start of the culture, and the amount of aeration and the agitation rotational speed were gradually increased until the maximum aeration amount was 240 m$^3$/hr (air flow rate (=Vs): 0.0262 m/sec) and the maximum agitation power (=P/V) was 1098 W/m$^3$, by hour 48 of the culture. Values of the parameters at the high aeration-agitation level were calculated as follows.

$$(P/V)^{0.95}:773.8[(W/m^3)^{0.95}]$$

$$Vs^{0.67}:0.0871[(m/sec)^{0.67}]$$

$$KLA(=(P/V)^{0.95}VS^{0.67}):67.4[(W/m^3)^{0.95} \cdot (m/sec)^{0.67}] \quad \text{(Expression 14)}$$

The main culture was performed for 376 hours while adding glucose at some point(s) during the culture. As a result, the concentration of produced mead acid was 6.0 g/L at the end of culture.

INDUSTRIAL USABILITY

At least any one of arachidonic acid, which particularly plays an important role as a nutrient for suckling infants, or a compound (e.g., fats, oils, etc.) containing arachidonic acid as a constituent fatty acid, can be efficiently and stably produced. Therefore, the present invention is useful for production of beverages, therapeutic nutrient foods, feeds, pharmaceuticals, and the like which contain these materials.

What is claimed is:

1. A method of producing a highly unsaturated fatty acid by culturing a strain of *Mortierella alpina* capable of producing the highly unsaturated fatty acid in a culture medium containing at least a carbon source and a nitrogen source, using an aeration-agitation culture device capable of adjusting and controlling an agitation power and an aeration amount, the method comprising:

performing mechanical agitation after start of a main culture, wherein the agitation power per unit liquid amount is 30-269 (W/m$^3$)thereby promoting a transformation of *M. alpina* cells from a form of a pulp-shaped hypha to a pellet-shaped form, and wherein the main culture is started by inoculating a seed culture; and immediately before dissolved oxygen concentration value decreases to about 50% or 12 to 24 hours after start of the main culture, increasing aeration or agitation by adjusting and controlling at least any one of the maximum aeration amount and a maximum power required for agitation to a range which satisfies that KLA (=(P/V)$^{0.95}$Vs$^{0.67}$) is 59-282, an air flow rate parameter Vs$^{0.67}$ is 0.075-0.191, and a required agitation power parameter (P/V)$^{0.95}$ is 282-2169, where P represents power required for agitation (W), V represents a liquid amount (m$^3$), and Vs represents an air flow rate (m/sec), thereby producing the highly unsaturated fatty acid from the main culture.

2. The method according to claim 1, wherein the highly unsaturated fatty acid is arachidonic acid.

3. A method of producing a compound containing a highly unsaturated fatty acid by culturing a strain of *Mortierella alpina* capable of producing the compound containing the highly unsaturated fatty acid in a culture medium containing at least a carbon source and a nitrogen source, using an aeration-agitation culture device capable of adjusting and controlling an agitation power and an aeration amount, the method comprising:

performing mechanical agitation after start of a main culture, wherein the agitation power per unit liquid amount is 30-269 (W/m$^3$) thereby promoting a transformation of *M. alpine* cells from a form of pulp-shaped hypha to a pellet-shaped form, and wherein the main culture is started by inoculating a seed culture; and immediately before dissolved oxygen concentration value decreases to about 50% or 12 to 24 hours after start of the main culture, increasing aeration or agitation by adjusting and controlling at least any one of the maximum aeration amount and a maximum power required for agitation to a range which satisfies that KLA (=(P/V)$^{0.95}$Vs$^{0.67}$) is 59-282, an air flow rate parameter Vs$^{0.67}$ is 0.075-0.191, and a required agitation power parameter (P/V)$^{0.95}$ is 282-2169, where P represents power required thr agitation (W), V represents a liquid amount (m$^3$), and Vs represents an air flow rate (m/sec), thereby producing the compound containing the highly unsaturated fatty acid from the main culture.

4. The method according to claim 3, wherein the highly unsaturated fatty acid is arachidonic acid.

5. The method according to claim 1, wherein (P/V)$^{0.95}$ is in the range of 282-2169 and Vs$^{0.67}$ is in the range of 0.075-0.191 after increasing aeration or agitation.

6. The method according to claim 1, wherein (P/V)$^{0.95}$ is in the range of 282-2169 and KLA (=(P/V)$^{0.95}$Vs$^{0.67}$) is in the range of 59-282 after increasing aeration or agitation.

7. The method according to claim 3, wherein (P/V)$^{0.95}$ is in the range of 282-2169 and Vs$^{0.67}$ is in the range of 0.075-0.191 after increasing aeration or agitation.

8. The method according to claim 3, wherein (P/V)$^{0.95}$is in the range of 282-2169 and KLA (=(P/V)$^{0.95}$Vs$^{0.67}$) is in the range of 59-282 after increasing aeration or agitation.

* * * * *